United States Patent
Rudnick et al.

(10) Patent No.: US 6,986,780 B2
(45) Date of Patent: Jan. 17, 2006

(54) SURGICAL ELEMENT DELIVERY SYSTEM AND METHOD

(75) Inventors: James J. Rudnick, Mahwah, NJ (US); Scott Ciarrocca, Stockton, NJ (US); Robert J. Tannhauser, Bridgewater, NJ (US); John P. Collier, Franklin Lakes, NJ (US)

(73) Assignee: Ethicon, Inc., Somerville, NJ (US)

( * ) Notice: Subject to any disclaimer, the term of this patent is extended or adjusted under 35 U.S.C. 154(b) by 165 days.

(21) Appl. No.: 10/400,108

(22) Filed: Mar. 26, 2003

(65) Prior Publication Data

US 2003/0212417 A1 Nov. 13, 2003

Related U.S. Application Data

(60) Provisional application No. 60/367,900, filed on Mar. 26, 2002.

(51) Int. Cl.
*A61B 17/06* (2006.01)

(52) U.S. Cl. ............................ 606/222; 606/1; 206/380
(58) Field of Classification Search ................ 206/380; 606/222–233
See application file for complete search history.

(56) References Cited

U.S. PATENT DOCUMENTS

| | | |
|---|---|---|
| 749,934 A | 1/1904 | Hollister |
| 779,338 A | 1/1905 | Williams |
| 805,948 A | 11/1905 | Evans |
| 1,334,916 A | 3/1920 | Lukens |
| 4,574,957 A | 3/1986 | Stead |
| 4,621,640 A | 11/1986 | Mulhollan et al. |
| 4,651,753 A | 3/1987 | Lifton |
| 5,195,533 A | 3/1993 | Chin et al. |
| 5,234,634 A | 8/1993 | Janoff et al. |
| 5,524,634 A | 6/1996 | Turkel et al. |
| 5,526,822 A | 6/1996 | Burbank et al. |
| 5,573,109 A | 11/1996 | Isacson |
| 5,601,585 A | 2/1997 | Banik et al. |
| 5,609,827 A | 3/1997 | Russell et al. |
| 5,810,744 A | 9/1998 | Chu et al. |
| 5,823,971 A | 10/1998 | Robinson et al. |
| 5,928,164 A | 7/1999 | Burbank et al. |
| 5,980,468 A | 11/1999 | Zimmon |
| 6,110,127 A | 8/2000 | Suzuki |
| 6,142,957 A | 11/2000 | Diamond et al. |
| 6,241,687 B1 | 6/2001 | Voegele et al. |
| 6,258,327 B1 | 7/2001 | Tatum |
| 6,322,522 B1 | 11/2001 | Zimmon |
| 6,330,965 B1 | 12/2001 | Milliman et al. |
| 6,468,227 B2 | 10/2002 | Zimmon |
| 6,632,182 B1 | 10/2003 | Treat |
| 2001/0023352 A1 | 9/2001 | Gordon et al. |
| 2001/0023353 A1 | 9/2001 | Gordon et al. |
| 2004/0129591 A1 * | 7/2004 | Koseki ...................... 206/380 |

OTHER PUBLICATIONS

International Search Report dated Mar. 29, 2004, for corresponding PCT/US03/09297.
PCT Search Report dated Sep. 4, 2003, for APPN. No. PCT/US03/09365.

* cited by examiner

*Primary Examiner*—Beverly M. Flanagan
*Assistant Examiner*—Matthew J Kasztejna

(57) ABSTRACT

A surgical element carrier and method for use is provided, wherein the surgical element carrier includes a housing dimensioned to contain therein a plurality of surgical elements, and dimensioned for insertion through a surgical port used in minimally invasive surgeries. The housing further includes a first housing portion and a second housing portion movable relative to the first housing portion between a closed position wherein the surgical elements are substantially surrounded by the housing, and an open position wherein the surgical elements are at least partially exposed and removable from the housing.

25 Claims, 19 Drawing Sheets

FIG. 1c
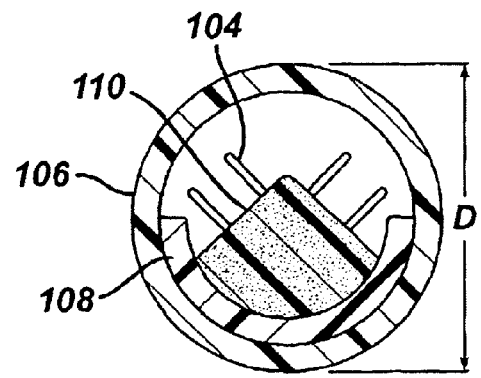
FIG. 1d
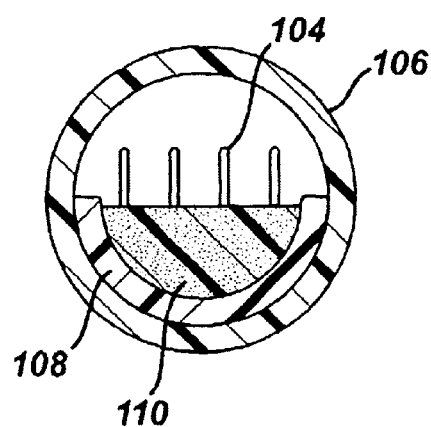
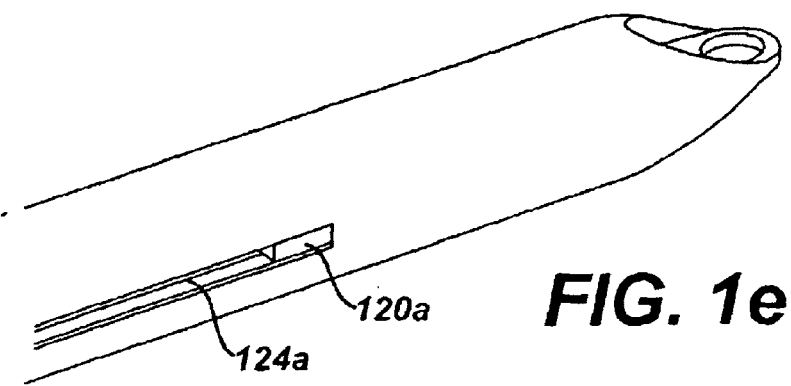
FIG. 1e

SURGICAL ELEMENT DELIVERY SYSTEM AND METHOD

CROSS REFERENCE TO RELATED APPLICATIONS

The present application claims the benefit of earlier filed U.S. provisional application Ser. No. 60/367,900, filed on Mar. 26, 2002, the contents of which are incorporated herein by reference.

FIELD OF THE INVENTION

The present invention relates to a system and method for introducing into a surgical site at one time a plurality of surgical devices, instruments or other objects, that may be used by a surgeon during surgery. The system and method has particular application to minimally invasive surgery, such as endoscopic or laporoscopic surgery, and enables introduction of the plurality of devices into the surgical site through the cannula or other surgical port through which the surgery is performed.

BACKGROUND OF THE INVENTION

In the medical world, an increasing number and type of surgeries are being performed using minimally invasive techniques. Typically, these procedures involve making one or more relatively small incisions in the patient in proximity to the surgical target. A cannula or other type of surgical port (hereinafter referred to generally as a "surgical port") is inserted into the patient through the incision to form a conduit through which the surgeon can access the surgical site. The surgeon then performs the entire surgery from the exterior of the patient's body by manipulating surgical devices and instruments through the surgical port.

Multiple different surgical instruments, such as needle holders, graspers, scissors, clip appliers etc., are often used during the course of a surgical procedure. These procedures also frequently require surgical sutures, clips, anchors or the like to mend or repair tissue or organs. For the purposes of this disclosure, the term "surgical elements" is used to generally refer to all devices, instruments or other objects that are used within a patient's body during surgery. Because only small incisions are made in the body for minimally invasive surgery, all surgical elements must be introduced into the surgical site through the surgical port as needed. For example, if the procedure requires removal of tissue and subsequent mending of the injured area, a surgeon may first insert through the surgical port a surgical tool having a cutting tip to perform the necessary cutting. This tool is subsequently removed from the patient and may be exchanged for another tool having a grasping element at the end that can hold a needle and perform necessary suturing. This tool, along with the suture and needle, must then be inserted into the surgical site through the surgical port. If another suture is required, the tool must be removed through the surgical port, and reintroduced into the surgical site with another suture. Thus, every time a new instrument or device is needed at the surgical site, it must be separately introduced through the surgical port.

Removal and reintroduction of surgical instruments and devices into the surgical site is time consuming. Further, inserting a surgical tool that is grasping an element such as a suture is difficult, as the diameter of the surgical port is relatively small, typically in the order of 5–25 mm. The needle, on the other hand, may be curved and can have a length and width of up to 20 mm and 12 mm respectively. Often, the surgeon must grab the needle in one manner to be able to pass it through the surgical port, then, once inside the patient, must re-grasp it in another orientation to perform the suturing. To do this, it is often necessary to manipulate the extremely sharp needle directly on the surface of the tissues until it is in the correct orientation to be grasped. As indicated, this entire process of removing the tool and reintroducing another suture and needle must be performed when another suture is needed.

For each suture, once the suturing has been completed, the needle must be removed from inside the patient. Damage to the cannula caused by the sharp needle is a problem that is frequently encountered. In particular, the airtight seal within the cannula that prevents gas from escaping or entering the surgical site can easily be damaged by the sharp needles. In sum, the introduction of surgical instruments and devices into the surgical site is a difficult and time consuming aspect of minimally invasive surgery.

These issues are compounded when robotics are used in conjunction with minimally invasive surgery. In robotic surgery, robotic arms perform the actual surgery, with the robotic arms being remotely controlled by the surgeon via a computer or the like. Removal of the robotic arms from the surgical site via a surgical port is undesirable, as the surgeon's viewpoint provided by a video camera is internal surgical space. Complete withdrawal of the instrument requires secondary team members to reposition the instrument back through the surgical port and back into the surgeon's field of view.

Accordingly, it is desirable to achieve a system and method for introducing a plurality of surgical elements into surgical site at one time, particularly in conjunction with performing minimally invasive surgery. It is further desirable to provide a method for performing such surgery utilizing this system and method.

SUMMARY OF THE INVENTION

The present invention provides a surgical element carrier including a housing dimensioned to contain therein a plurality of surgical elements, and dimensioned for insertion through a surgical port used in minimally invasive surgeries. The housing further includes a first housing portion and a second housing portion movable relative to the first housing portion between a closed position wherein the surgical elements are substantially surrounded by the housing, and an open position wherein the surgical elements are at least partially exposed and removable from the housing.

In one embodiment, the first housing portion is slidably engaged with the second housing portion and slidable relative to the second housing portion between the closed and open positions. In another embodiment, the first housing portion is pivotably coupled with the second housing portion and pivotable between the open and closed positions. In yet another embodiment, the first housing portion is pivotably coupled to the second housing portion by at least one hinge, and when the first housing portion is in the open position, the at least one hinge is biased toward the open position.

The housing may be substantially cylindrical in shape, with a length and a diameter that is less than a diameter of the surgical port. The surgical elements optionally may be sutures having a needle attached thereto, or surgical tips for an endoscopic surgical instrument. In yet another embodiment, the housing is flexible.

In an alternate embodiment, the surgical element carrier further includes a securing device at one end thereof, which may be a clamp, or a pointed element capable of penetrating tissue.

In yet another embodiment, the surgical element carrier further includes a receiving element for receiving and maintaining in position the surgical elements, which may be made of a foam material. In another embodiment, the surgical element carrier further includes a tether element extending from one end thereof having a length sufficient to extend from a surgical site within a patient's body, through the surgical port and to an exterior of the patient's body.

Also provided is a surgical element carrier having a housing for transporting a plurality of surgical elements through a surgical port designed for use in a minimally invasive surgical procedure. The housing has a length and a diameter, wherein the diameter is less than a diameter of the surgical port. The housing is configured to partially surround the surgical elements, and has an aperture therein of a sufficient size and shape to enable the surgical elements to be removed from the carrier by an endoscopic surgical instrument.

A method is also provided for introducing a plurality of surgical elements into a surgical site during a minimally invasive surgical procedure. The method includes providing a surgical element carrier having a housing containing therein a plurality of surgical elements. The housing has a first housing portion and a second housing portion movable relative to the first housing portion between a closed position wherein the surgical elements are substantially surrounded by the housing and an open position wherein the surgical elements are at least partially exposed and removable from the housing. The method further includes inserting the housing having the plurality of surgical elements therein into the surgical site through a surgical port, selectively removing from at least one surgical element from the surgical element carrier while the surgical element carrier is within the surgical site, using the at least one surgical element during the minimally invasive surgical procedure, and removing the surgical element carrier from the surgical site through the surgical port.

In one embodiment the method further includes, following the inserting step, opening the surgical element carrier to expose the surgical elements contained therein.

The housing may further include a first housing portion and a second housing portion movable relative to the first housing portion, wherein the first housing portion is slidably engaged with the second housing portion and slidable relative to the second housing portion between a closed wherein the housing substantially surrounds the surgical elements and an open position wherein the surgical instruments are at least partially exposed and can be removed from the housing. In another embodiment the housing may further include a first housing portion and a second housing portion movable relative to the first housing portion, wherein the first housing portion is pivotably coupled with the second housing portion and pivotable relative to the second housing portion between a closed wherein the housing substantially surrounds the surgical elements and an open position wherein the surgical instruments are at least partially exposed and can be removed from the housing.

BRIEF DESCRIPTION OF THE FIGURES

For a better understanding of the present invention, reference is made to the following detailed description of an exemplary embodiment considered in conjunction with the accompanying drawings, in which:

FIG. 1c is a cross-sectional view of the carrier of FIGS. 1a and 1b;

FIG. 1d is a cross-sectional view of another embodiment of a carrier according to the present disclosure;

FIG. 1e is an enlarged view of the distal end region of the carrier of FIG. 1a.

DETAILED DESCRIPTION OF THE FIGURES

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

According to the present disclosure, a surgical carrier is provided for transporting or carrying a plurality of surgical elements into a surgical site within a patient. These surgical elements may be any type of instrument, device or other object that may be used or needed during a surgical procedure, as will be described more fully below. For example, the surgical carrier may carry a plurality of sutures and needles of any size or length, clips, anchors, staples or any other type of device used to repair or alter body tissue at the surgical site. The surgical carrier could also carry a plurality of different types of tools, instruments or other objects used during surgery, such as graspers, clip appliers, scissors or the like.

Figure 1A:
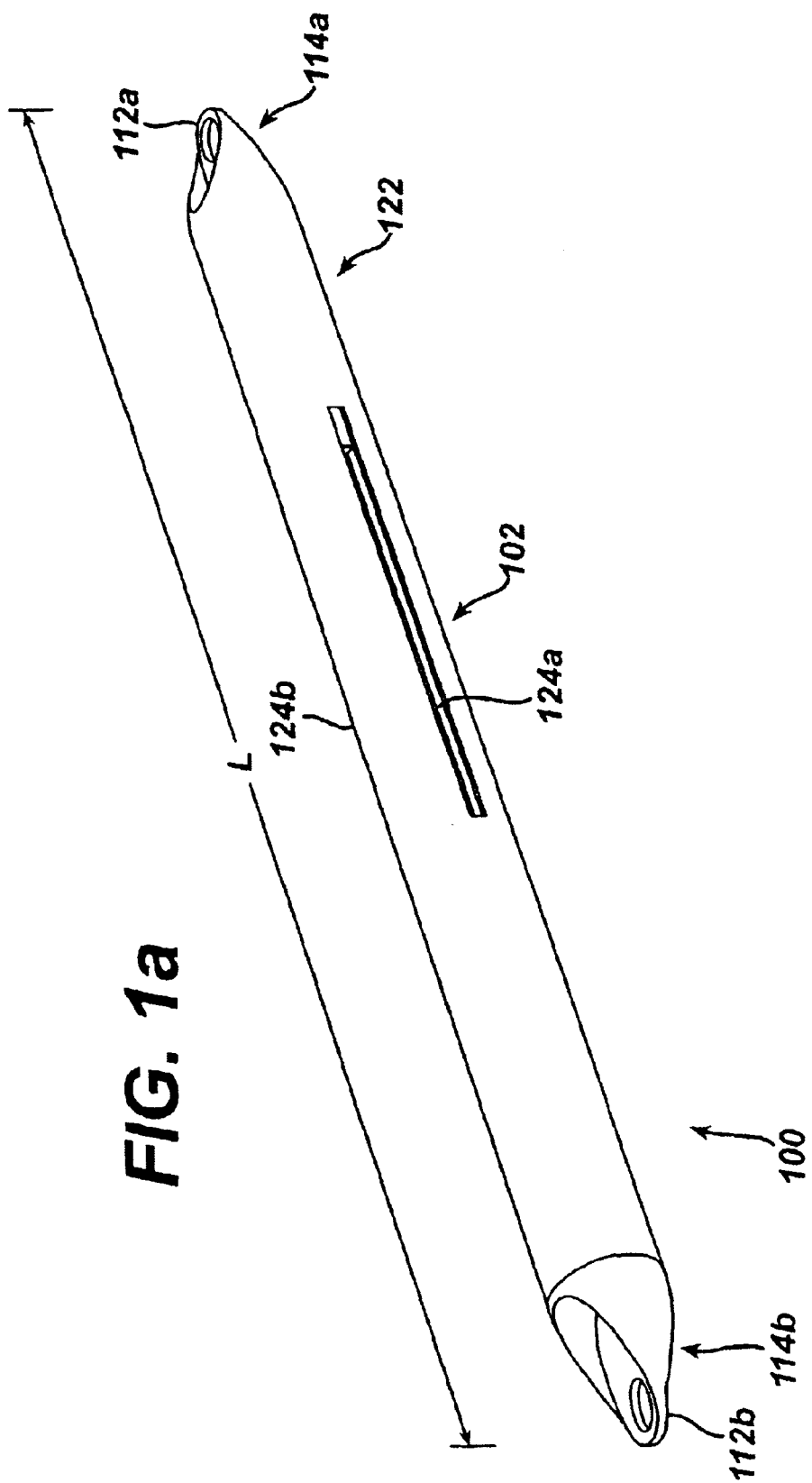
FIG. 1a illustrates one embodiment of a carrier according to the present disclosure in the closed position.
Figure 1B:
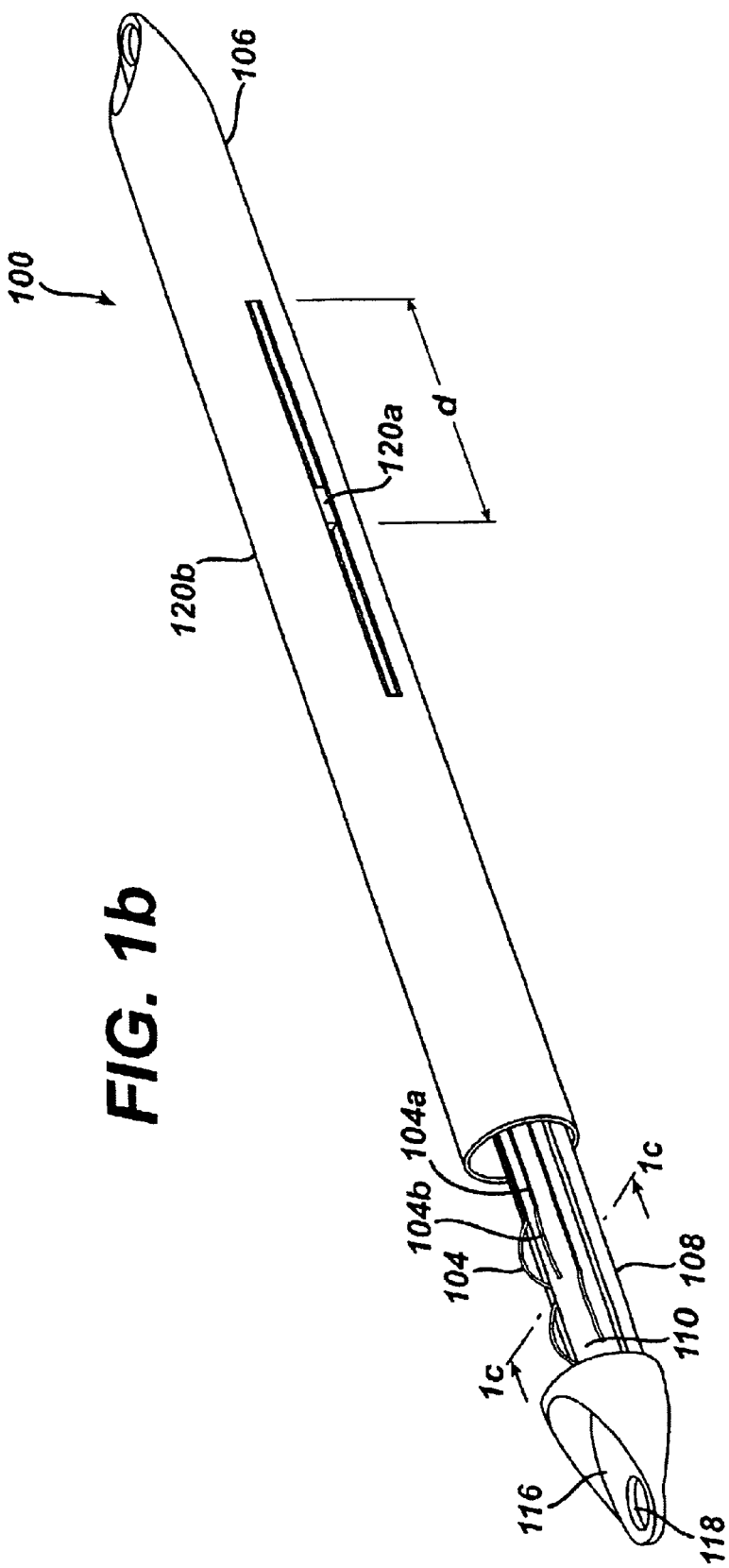
FIG. 1b illustrates the carrier of FIG. 1a in the open position.

One embodiment of a surgical carrier according to the present disclosure is illustrated in FIGS. 1a–1c. The surgical carrier 100 is substantially cylindrical in overall shape, as illustrated in FIG. 1a, and has an outer diameter D that is less than the inner diameter of a surgical port through which the minimally invasive surgery is performed. In a preferred embodiment, the diameter is slightly less than 10 or 12 mm to allow passage through surgical ports with internal diameters of 10 and 12 mm respectively. The length L of the carrier may vary, but should be small enough to both fit into the surgical site, and be manipulated therein without damaging surrounding tissue or organs. In one embodiment, the length L is approximately 11 cm, but could range from less than 5 to greater than 15 cm depending upon the configuration required to deliver the surgical devices.

The carrier illustrated in FIG. 1a includes a housing 102 that substantially surrounds and protects the surgical elements 104 (in this case sutures) within it. In this embodiment, the housing includes an outer housing member 106 and a base housing member 108 that is slidably received within the outer housing member and slidably relative to the outer housing member between a closed position (FIG. 1a) and an open position (FIG. 1b) in which the surgical elements are at least partially exposed and can be removed from and/or reinserted into the carrier. As shown, the surgical elements 104 are carried by the base portion, and are "parked" or held in place by a receiving element 110. The receiving element may be integral with the base portion, or may be a separate element that is secured to the base portion by any suitable means, such as an adhesive. The receiving element should be suitable for receiving and holding the surgical devices in place during normal movement of the carrier, such as during introduction of the carrier into the surgical site, and also allow removal and/or reinsertion of the surgical devices by a surgeon during the course of surgery.

In a preferred embodiment, the receiving element is a foam type element, such as Volara brand foam manufactured by Voltek, Inc., that, when viewed in cross-section, forms a triangular-like projection as shown in FIG. 1c. Multiple other configurations are also possible. For example, the receiving element may have a substantially flat surface, as shown in FIG. 1d, or have a plurality of projections and/or recesses between or within which surgical elements can be parked (see e.g., FIGS. 3d–3h). These projections and/or grooves may extend along any desired portion of the surgical device. Those skilled in the art will recognize that many configurations are possible without departing from the scope of the invention described herein.

The carrier of FIG. 1a also includes grasping portions 112a, 112b located at its first 114a and second 114b ends. The first grasping portion 112a is coupled to the outer housing portion 106, and the second grasping portion 112b is coupled to the base portion 108 to ensure that a surgeon, using a standard surgical tool such as a grasper, can grasp the respective grasping portions when the carrier is within the surgical site to slide the outer housing portion relative to the base portion between the open and closed positions shown in FIG. 1a and FIG. 1b respectively. According to one embodiment, the grasping portions include a substantially flat portion 116, with an aperture 118 therethrough. Many other configurations of the grasping portion are also suitable, such as a flat portion having a different configuration (see, e.g., FIG. 2a), with or without an aperture. The grasping portion(s) may also project from a side of the carrier rather than an end. Those skilled in the art will readily understand that numerous other configurations are also possible.

The embodiment illustrated in FIGS. 1a and 1b also includes first and second tab elements 120a, 120b projecting outwardly from the base portion at a location toward its distal end 122. The first and second tab elements project into first and second grooves 124a, 124b, respectively (see FIG. 1e) in the outer housing member that extend for a predetermined distance d along its length. The tabs slide within the respective grooves as the carrier transitions from the closed position of FIG. 1a to the open position of FIG. 1b. The length of the grooves should preferably be such that the carrier cannot be opened beyond a predetermined point. This point should be sufficient to enable a surgeon to access the surgical elements present within the carrier when in the open position, but also prevent the carrier from opening beyond a point necessary to achieve this access, and to prevent the base portion from being separated from the outer housing portion. The grooves may extend through the housing, but may also be recesses within the interior of the housing. Although one particular implementation is illustrated in FIGS. 1a and 1b, other suitable design configurations will be apparent to those skilled in the art. For example, tab elements may project from the outer housing portion into grooves in the base portion, or one tab element could be used.

The surgical devices that are received by the receiving element may be positioned in any suitable manner. In a preferred embodiment shown in FIGS. 1a–1c, where the surgical devices are sutures 104a attached to needles 104b, the needles are staggered to allow them to be grasped more easily by the surgeon. The sutures may have needles at a single end, or at both ends.

Figure 2A:
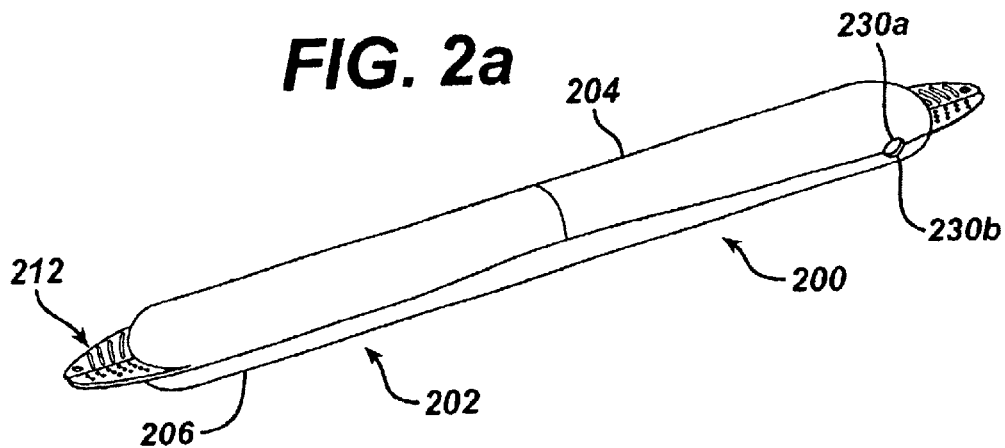
FIG. 2a illustrates another embodiment of a carrier according to the present disclosure in the closed position.

Other representative embodiments of the invention are illustrated in FIGS. 2a–8a and 10. FIGS. 2a–2c illustrate a carrier 200 including a substantially cylindrical shaped housing 202 having a lid portion 204 and a base portion 206 that are pivotably coupled to one another at a side edge 208, and pivotable relative to one another between a closed position (FIG. 2a) and an open position (FIG. 2b). The lid portion may have a length that is substantially equal to the length of the base portion so that when in the open position the entire contents of the carrier are exposed (see FIG. 2c). In the alternative, the lid portion may have a length that is equal to only a portion of the length of the base portion as shown in FIG. 2b. The first housing portion may also further include first and second lid portions 204a, 204b that are pivotably coupled to the base portion in the same manner as described above (FIG. 2c). This may be advantageous to enable a surgeon, depending on preference, to access either end of a double-needle suture 210.

Figure 2B:
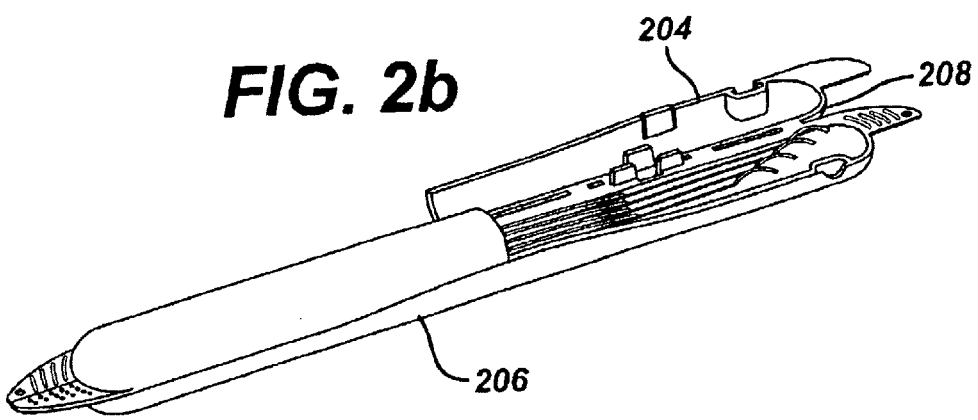
FIG. 2b illustrates the carrier of FIG. 2a in a partially open position.
Figure 2C:
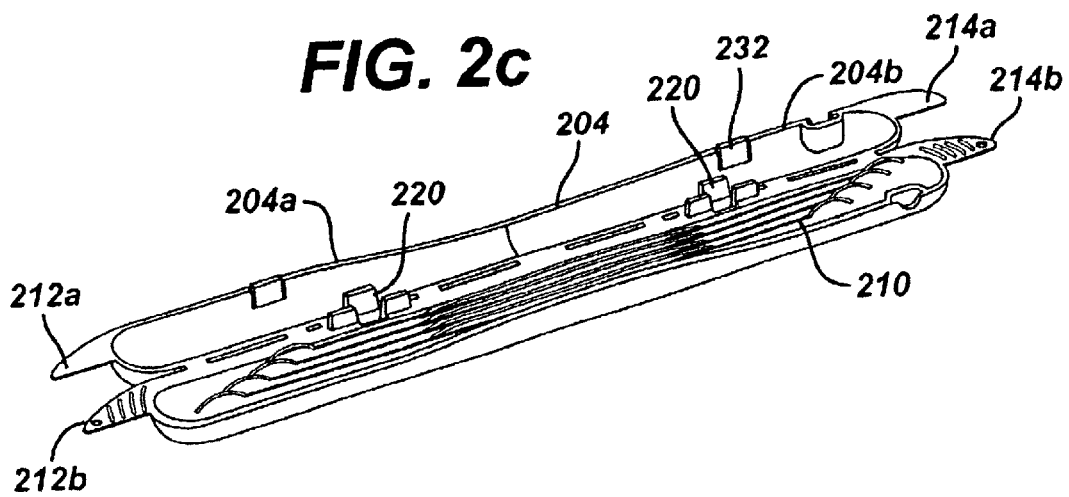
FIG. 2c illustrates the carrier of FIG. 2a in a fully open position.

The embodiment of FIGS. 2a–2c also include substantially flat grasping portions 212, 214 extending from each end. The grasping portions include a lid grasping portion 212a, 214a and a base grasping portion 212b, 214b that extend respectively from the lid portion and base portion. Preferably, the lid grasping portion and base grasping portion are at least partially offset, as illustrated, to facilitate opening of the lid portion. The grasping portion may further include raised projections 216, such as ridges, dots, or the like, to aid in grasping the ends.

Any suitable device may be used to pivotably couple the lid portion to the base portion, such as a hinge 220. In a preferred embodiment, a hinge element is used that, once the carrier is in the open position, it is biased to remain there. This will prevent the lid portion from unintentionally closing after the carrier has been opened within the surgical site, and will also provide additional stability for the carrier and a point of leverage when a surgeon is removing surgical elements from the carrier. Further, more than one hinge element may, of course, be utilized.

Figure 3A:
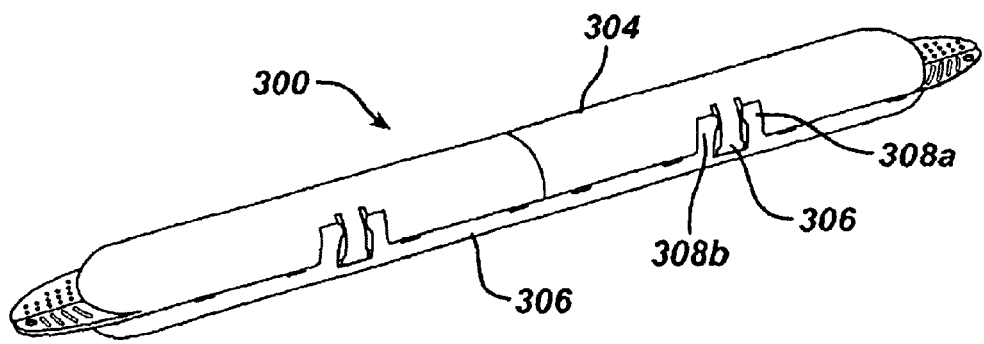
FIGS. 3a–3c illustrates in greater detail a hinge mechanism that can be used in conjunction with a carrier according to the present disclosure.
Figure 3B:
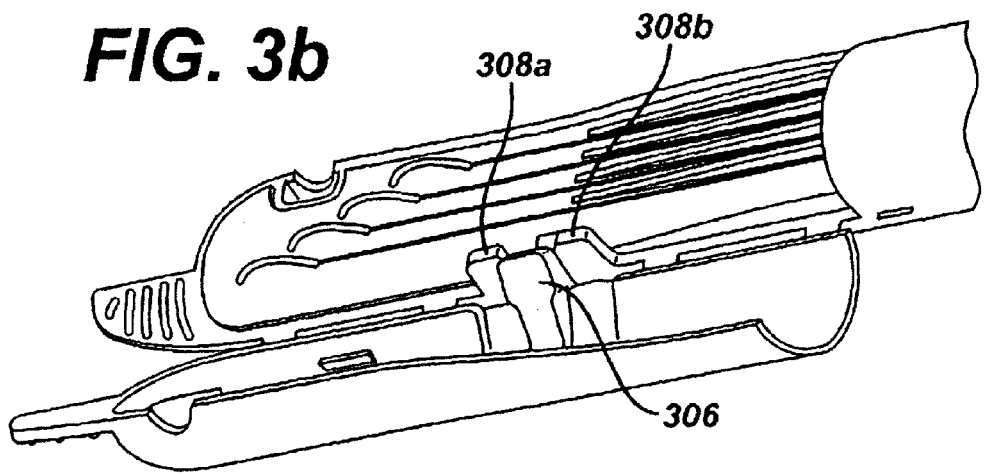
Figure 3C:
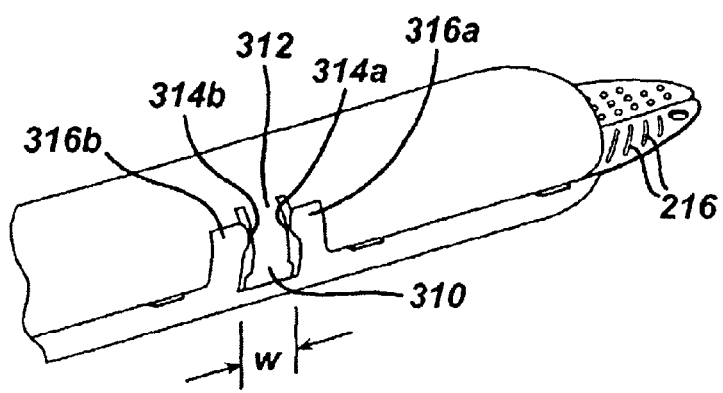
Figure 3D:
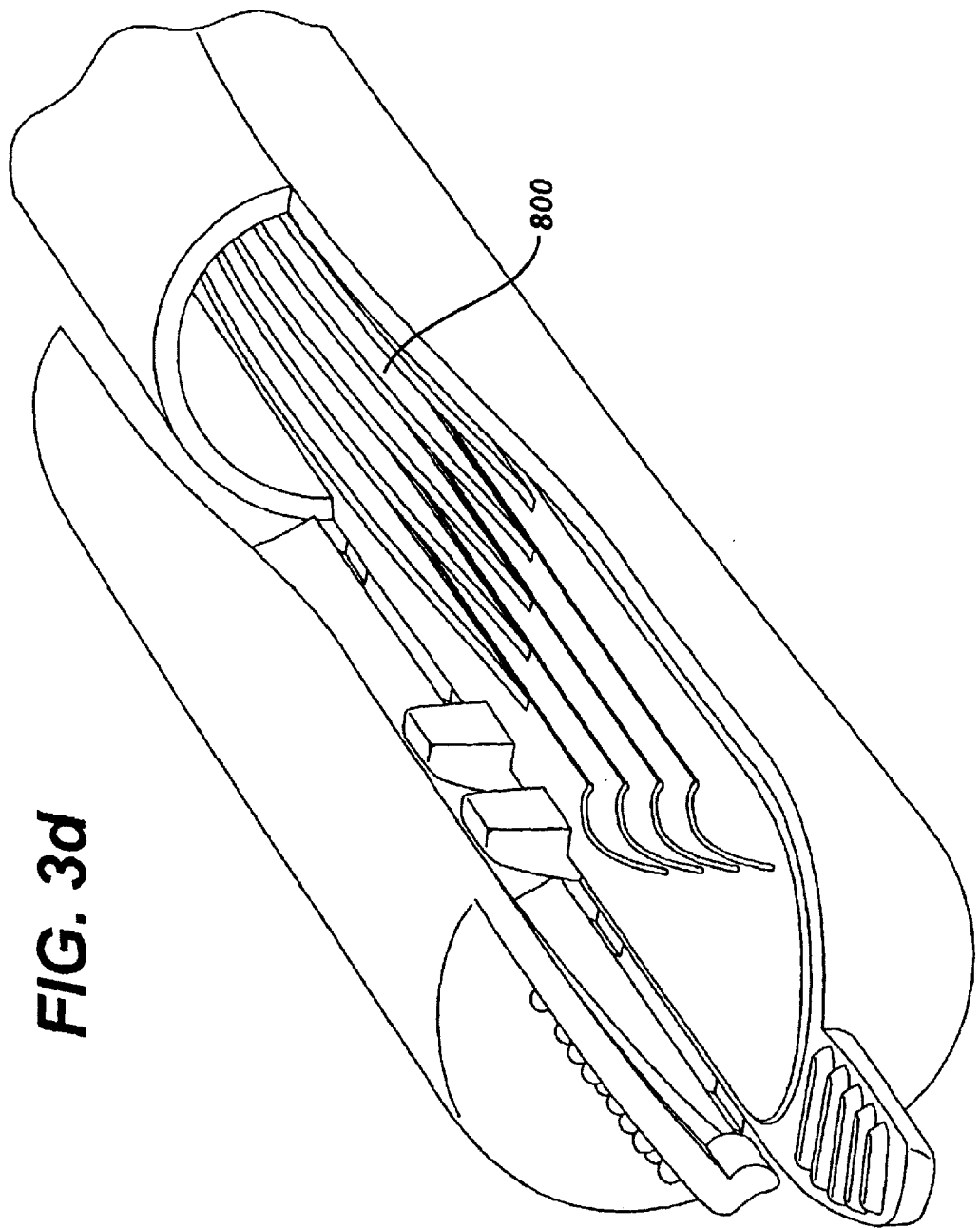
FIGS. 3d–3g illustrate a hinge mechanism that can be used in conjunction with a carrier according to the present disclosure at various stages of opening the carrier.
Figure 3E:
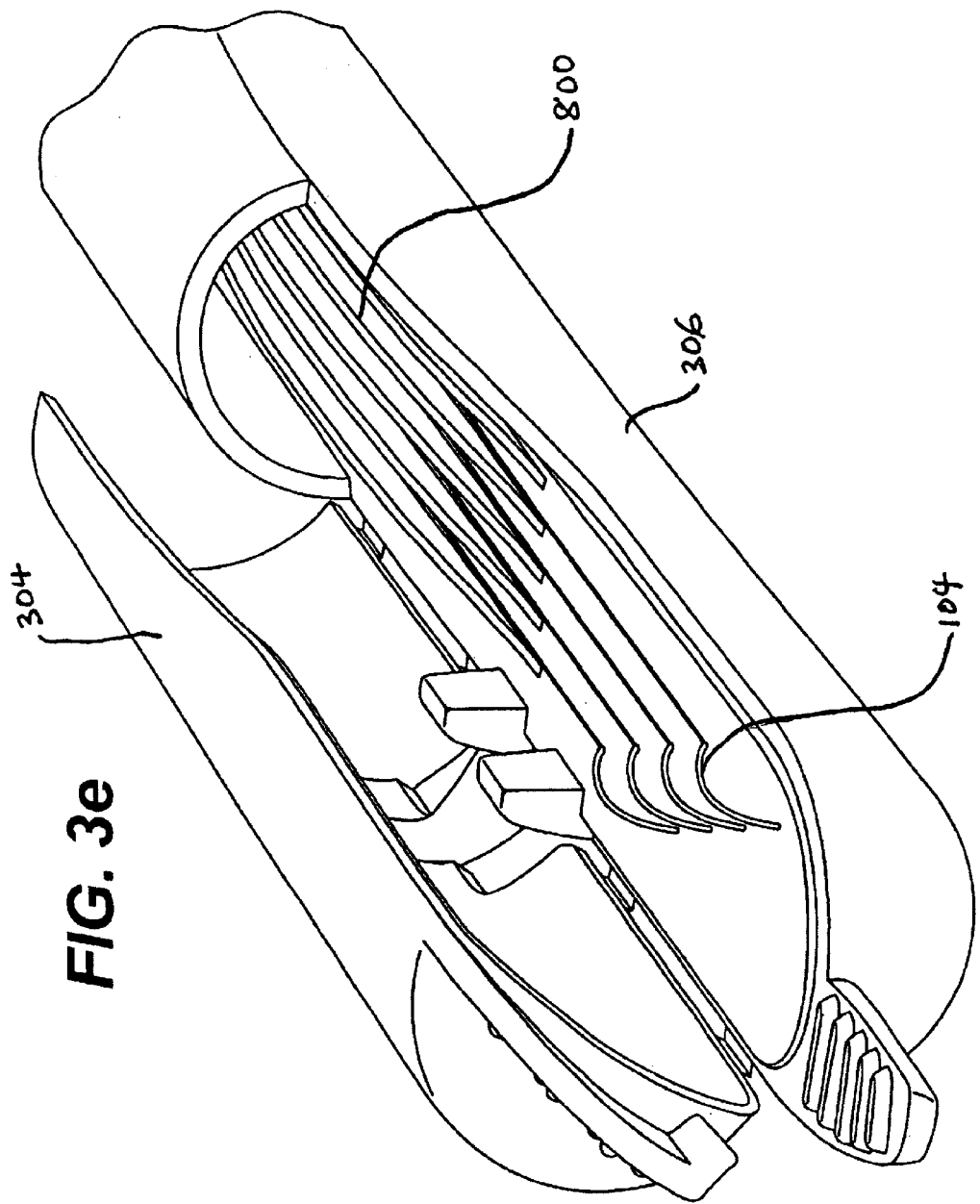
Figure 3F:
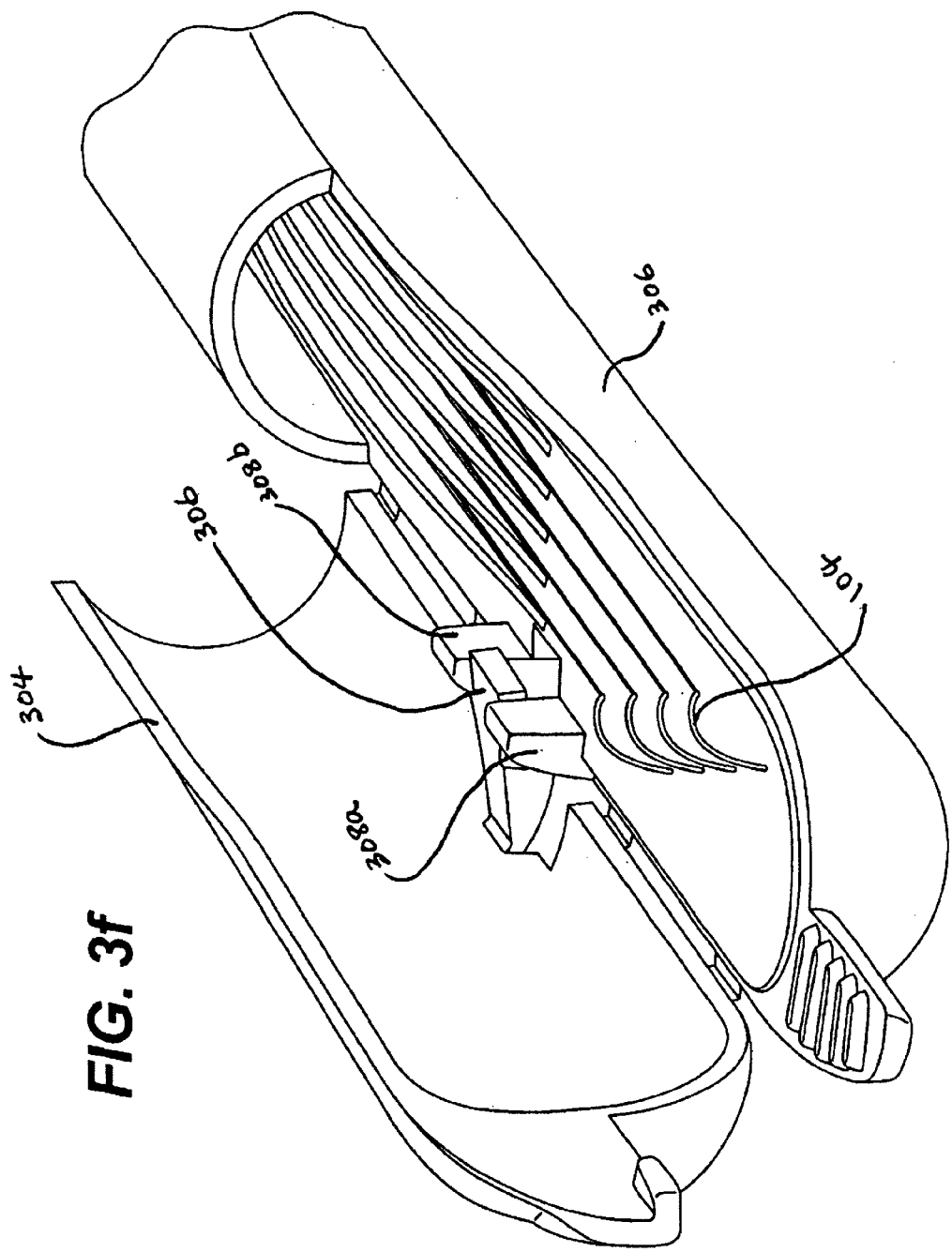
Figure 3G:
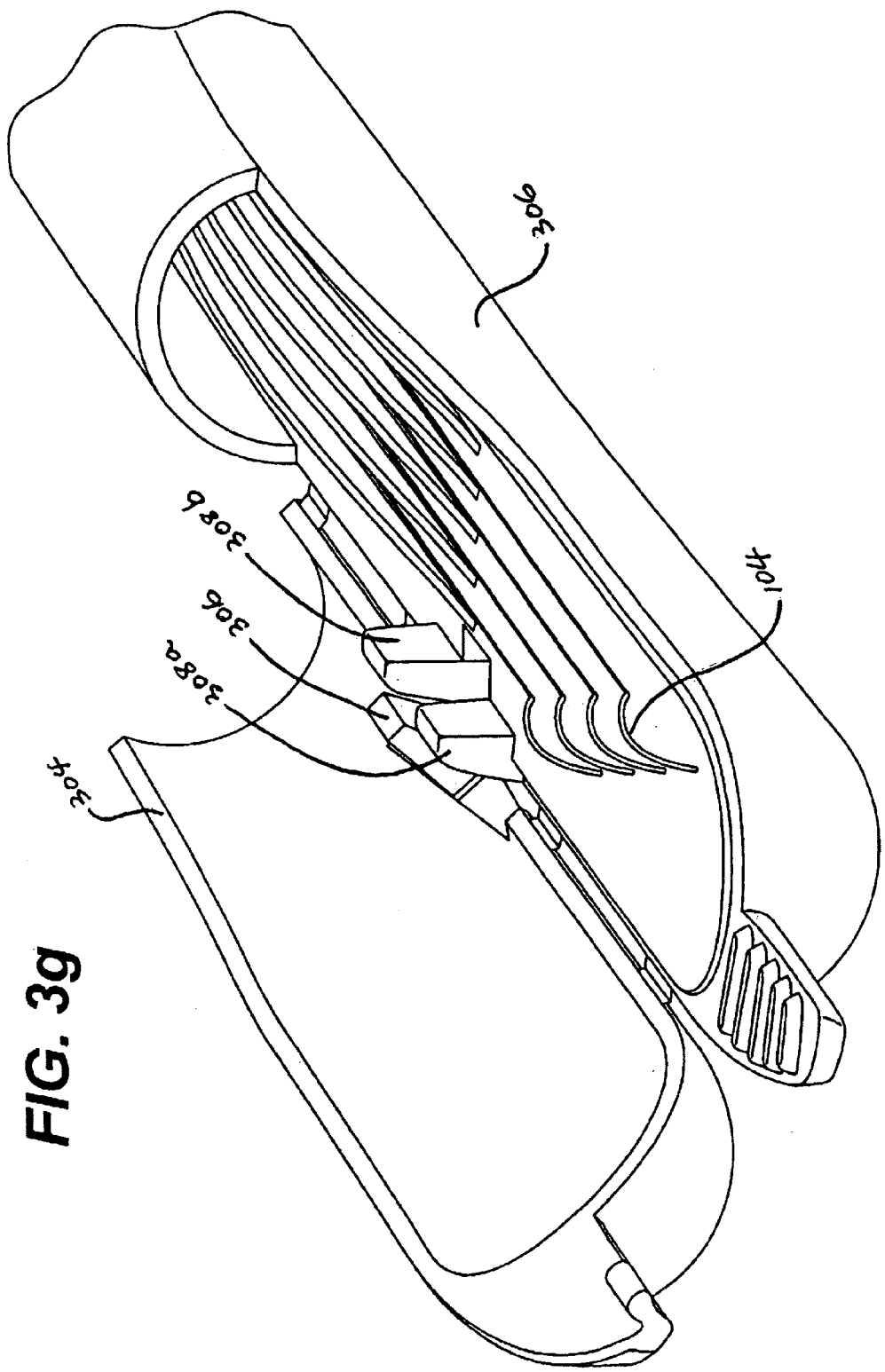
Figure 3H:
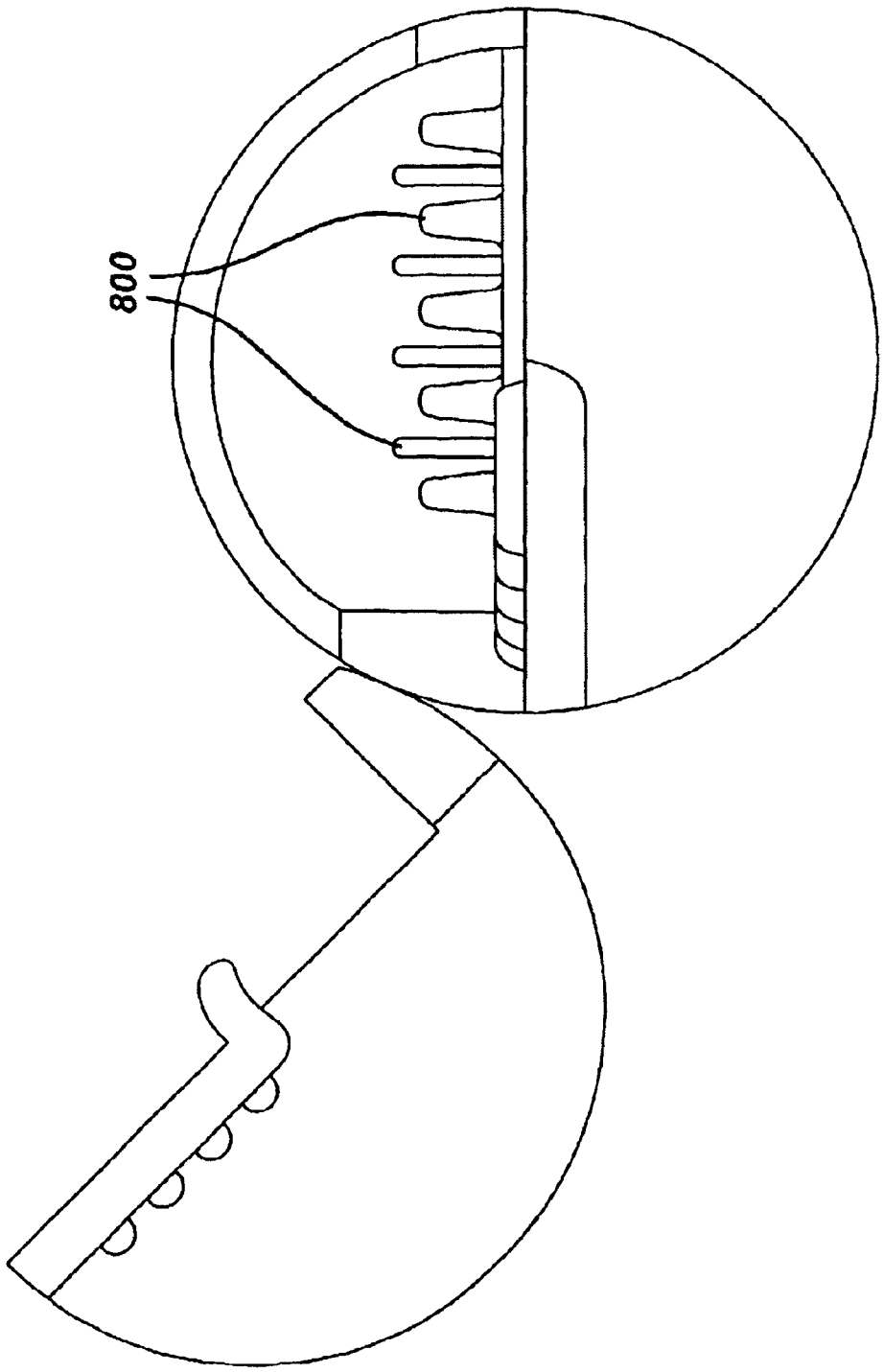
FIG. 3h is a cross-sectional view of another embodiment of a carrier according to the present disclosure.

A preferred embodiment of a hinge element is illustrated in more detail in FIGS. 3a–3g. The lid portion 304 of the carrier 300 includes a single hinge projection element 306 that is movably received between two hinge projection elements 308a, 308b on the base portion 306 of the housing When in the closed position, all hinge projection elements are substantially flush with the exterior surface of the housing, as shown in FIG. 3a. The hinge projection element 306 on the lid portion is a tab-like, having distal end 310 having a width w greater than the proximal end 312. The hinge projection elements of the base portion also have protrusions 314a, 314b at their distal ends 316a, 316b that extend inwardly toward the lid portion projection element. When the carrier is in the open position, these elements engage one another in a manner that prevents the lid portion from closing without some additional pressure being applied. Thus, the lid portion, once opened, is somewhat biased to stay open, preventing inadvertent closing of the carrier after it has been opened during surgery. FIGS. 3d–3g illustrate in greater detail the interaction of the lid hinge projection element 306 and the base portion hinge projection elements as the carrier transitions from the closed position to the open position.

In one embodiment, both the lid portion and the base portion of the housing further have recesses therein (230a, 230b respectively) that align with one another when the carrier is in the closed position, as shown in FIG. 2a, to facilitate opening of the carrier within the surgical site. The tip of a surgical instrument, such as a needle holder or graspers, can be inserted into the recess by the surgeon to pry open the carrier. The carrier may also include a tab element 232 on the lid portion that engages a groove or recess within the receiving element (or vice versa) to hold the carrier closed when in the closed position. This engagement should retain the carrier in the closed position under normal circumstances, but yield when a surgeon inserts an instrument into the recess to open the carrier as described above.

Figure 4A:
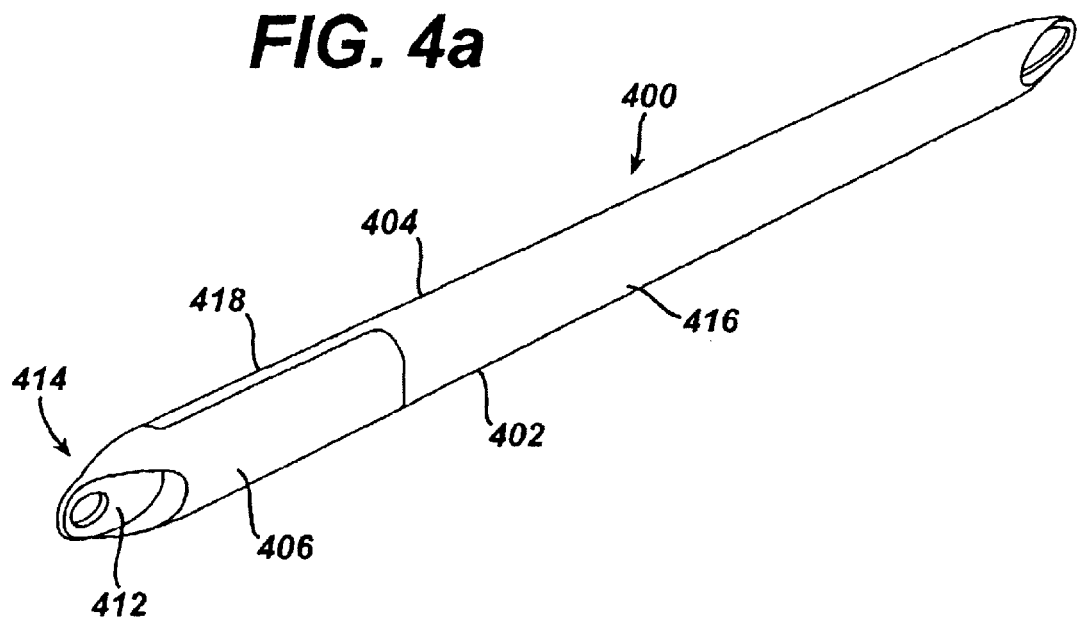
FIG. 4a illustrates yet another embodiment of a carrier according to the present disclosure in the closed position.
Figure 4B:
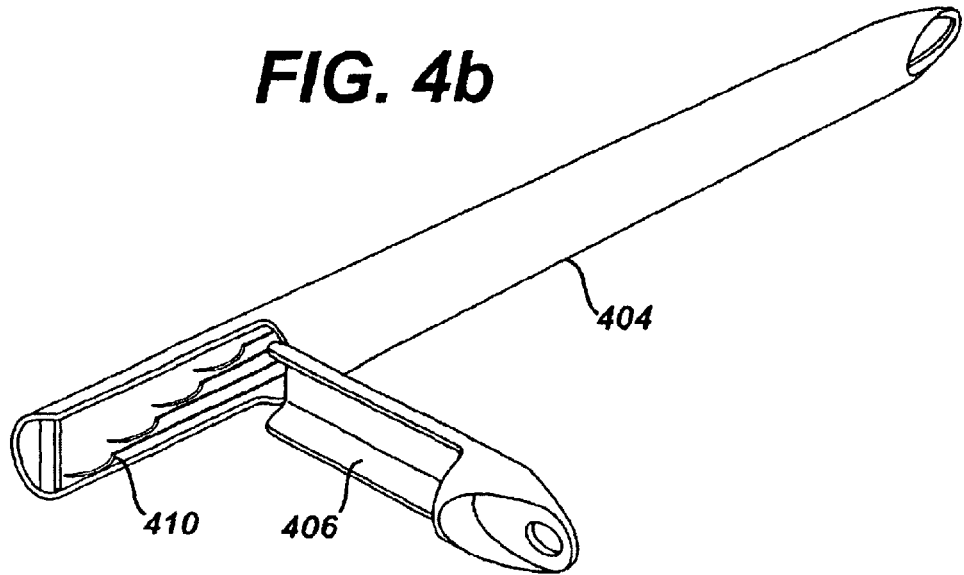
FIG. 4b illustrates the carrier of FIG. 4a in the open position.

Yet another embodiment of a carrier is illustrated in FIGS. 4a and 4b. FIG. 4a illustrates a carrier 400 having a housing 402 including a base portion 404 and a lid portion 406 pivotally coupled to the base portion by a hinge or any other suitable element. In this embodiment, the lid portion pivots perpendicularly outward relative to the base portion to the open position of the carrier (FIG. 4b) wherein the surgical elements 410 are removable by a surgeon. The grasping portion 412 at the first end 414 of the carrier is integral with the lid portion. In this embodiment, the exterior surface of the carrier includes first and second flat surfaces 416, 418 extending along at least a portion of the length of the carrier, however, the exterior of the carrier may have any other suitable configuration. For example, when taken in cross section, the exterior surface of the carrier may have many various configurations, from circular to polygons, or any combination thereof, so long as it can be inserted into the surgical site through a surgical port. In addition, fins or ribs can be added to the exterior to provide grasping sites for the instruments to facilitate positioning, opening, or closing.

As indicated, the housing must be made of a biocompatable material. One such suitable material is polypropylene, however, and of the range of biocompatible polymers could be utilized.

Figure 5A:
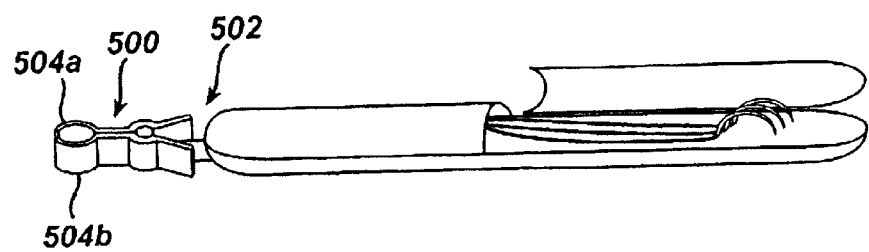
FIGS. 5a and 5b illustrate a carrier according to the present disclosure including a securing device.
Figure 5B:
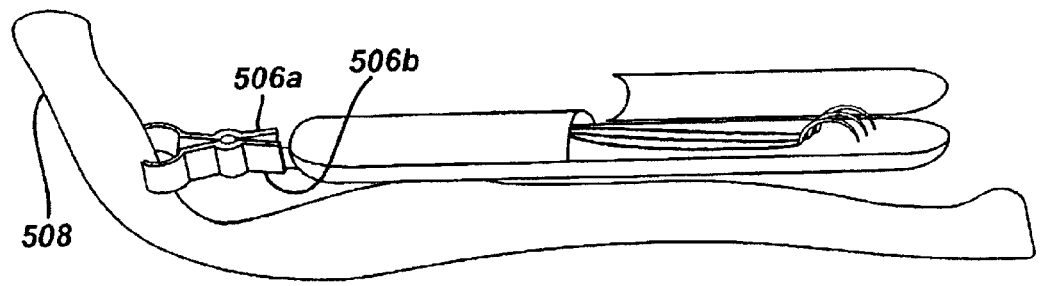

The carrier may also include an integrated securing device, such as a clamp or a pointed member or other configuration suitable for securing at least one end of the carrier to surrounding tissue in order to minimize movement of the carrier within the surgical site. One such securing device is illustrated in FIGS. 5a and 5b. The securing device 500 projects outwardly from a first end 502 of the carrier, and includes pinching elements 504a, 504b that are movable relative to one another, but under normal circumstances are biased closed as shown in FIG. 5a. The securing device also includes activation elements 506a, 506b that can be pressed to cause the pinching elements to separate from one another as shown in FIG. 5b. The surgeon can manipulate the activating elements to cause the securing device to engage selected surrounding tissue 508 or the like. Other securing devices can also be used within the spirit and scope of the invention described herein. For example, the securing device may simply have a configuration such that it can be at least partially imbedded into surrounding tissue.

Figure 6A:
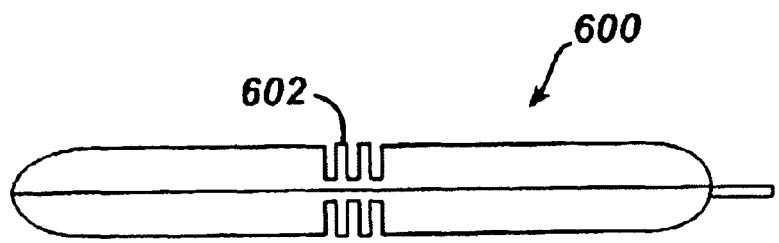
FIGS. 6a and 6b illustrate a carrier according to the present disclosure having a flexible housing.
Figure 6B:
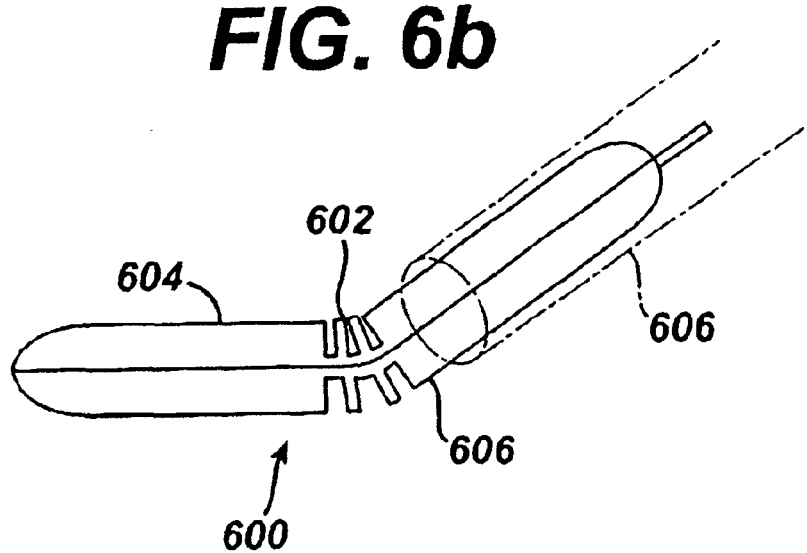

The housing of the carrier may also be flexible to enable easier insertion into and/or withdrawal from a surgical site in which space may be limited. As shown in FIGS. 6a and 6b, the housing 600 may include a flexing portion 602 to enable a first portion of the housing 604 to flex or pivot somewhat relative to a second portion of the housing 606, as shown in FIG. 6b, to facilitate introduction through a surgical port 606. Alternatively, the entire housing could be made of a flexible elastomer to facilitate withdrawal.

Figure 7A:
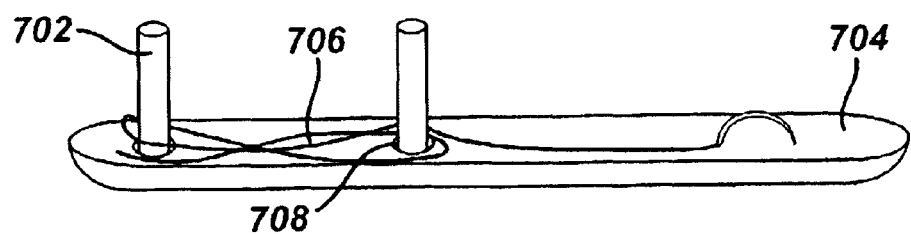
FIG. 7a illustrates a carrier according to the present disclosure including winding elements.
Figure 7B:
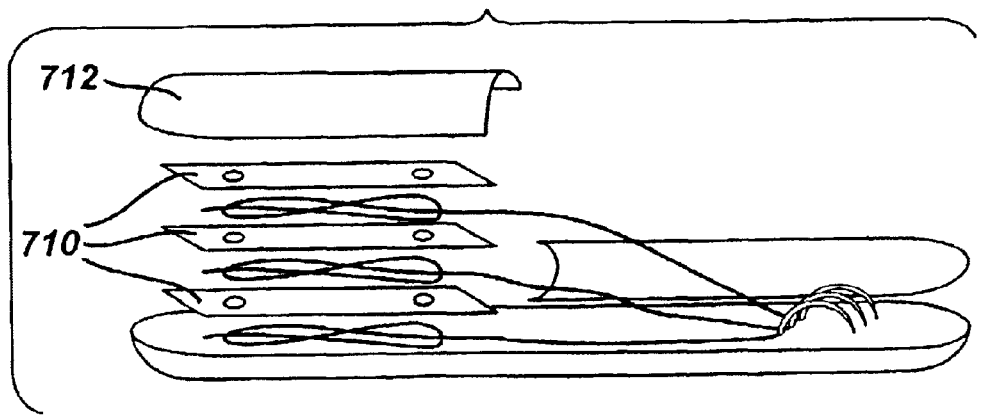
FIG. 7b illustrates a carrier according to the present disclosure including slip sheets between wound sutures.

The carrier may also include additional elements that assist in holding or arranging the surgical devices within the carrier. For example, FIG. 7a illustrates holes 708 that may be provided for the use of temporary winding pins 702 around which longer length sutures 706 could be wound. FIG. 7b illustrates slip sheets could be placed between the wound sutures, thus separating them and allowing for single strand dispensing. In this embodiment, the lid portion 712 would capture the wound sutures and slip sheets once the winding pins were withdrawn.

Figure 8A:
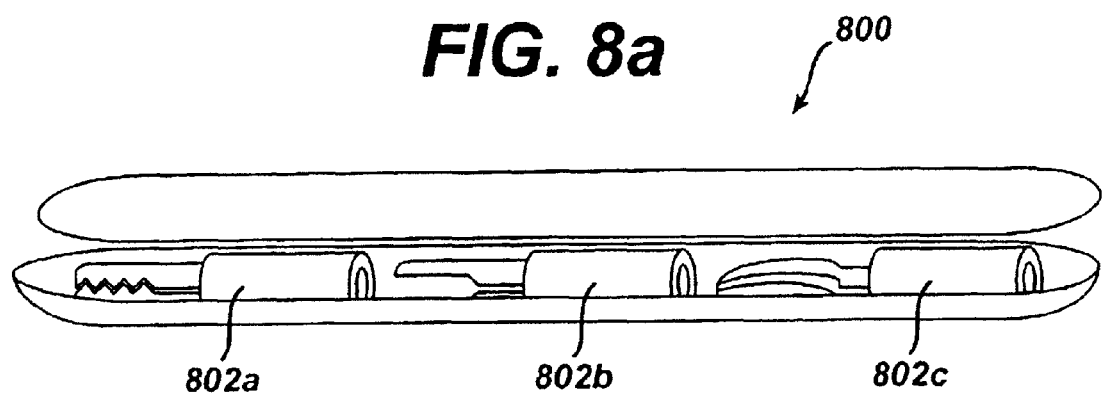
FIG. 8a illustrates a carrier according to the present disclosure carrying a plurality of surgical instruments.
Figure 8B:
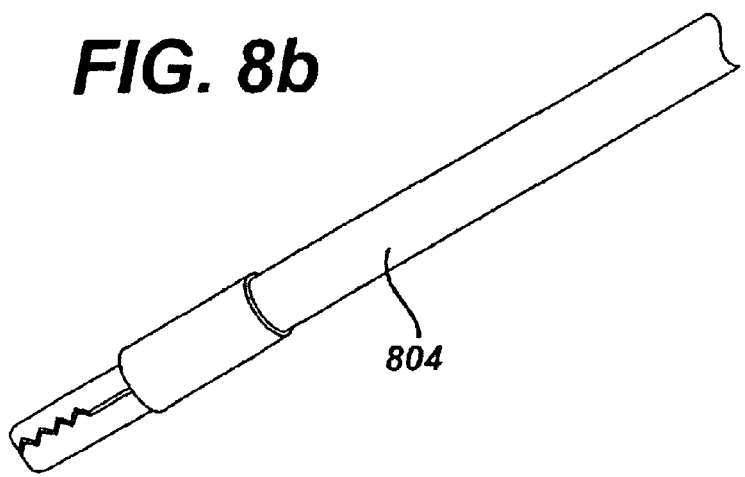
FIG. 8b illustrates a robotic arm having a surgical instrument tip attached thereto.

As indicated above, the carrier described herein can be used to introduce a plurality of surgical elements into the surgical site at one time. Although the figures discussed above illustrate only sutures, it is to be understood that any type of surgical tools, instruments or other devices can be carried within the disclosed carrier. For example, these could include any type of staples or clips, or various surgical instruments, as illustrated in FIGS. 8a and 8b. FIG. 8a illustrates a carrier 800 carrying a plurality of surgical instrument tips, such as a grasper or needle holder 802a, a clip applier 802b, and scissors 802c. Each of these surgical instrument tips may be designed to be removably and interchangeably coupled to the end of a surgical tool used by a surgeon, or the end of a robotic arm 804 that is used to perform robotic surgery as shown in FIG. 8b. Thus, the carrier enables multiple surgical instruments to be introduced into the surgical site at one time. The carrier can subsequently be opened by the surgeon, and the surgical instruments selected and used as needed. When another surgical instrument is needed, the former one is returned to the carrier, and the next one removed from the carrier and inserted into the robotic arm or other surgical instrument. Thus, the disclosed carrier eliminates, or greatly reduces the need to remove the robotic arm or other surgical instrument during the course of the surgery.

Figure 10:
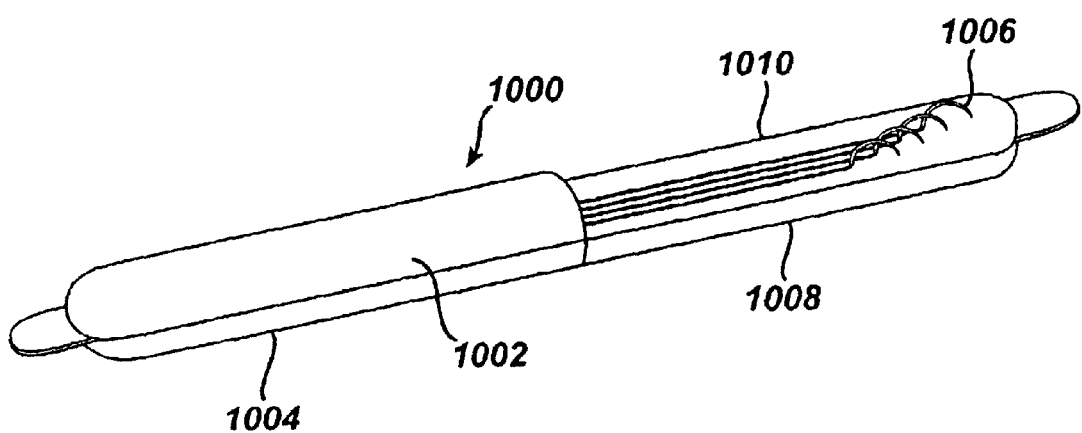
FIG. 10 illustrates yet another embodiment of a carrier according to the present disclosure wherein the surgical elements are at least partially exposed.

FIG. 10 illustrates yet another embodiment of a surgical carrier according to the present disclosure. The carrier 1000 includes a housing 1002 that includes a first housing portion 1004 that partially surrounds the surgical elements 1006 and a second housing portion 1008 having an exposed side 1010 such that the surgical elements are also partially exposed at all times. The exposed side of the second housing portion is such that the surgical elements are sufficiently exposed so that they can be selectively removed from the surgical carrier, as needed, by a surgeon. Thus, the surgical carrier of FIG. 10 provides a means by which a plurality of surgical elements can be introduced at one time into a surgical site, and provides sufficient protection for the surgical elements during such introduction, but allows easier access to the surgical elements once the carrier is within the surgical site.

Thus, the surgical carrier described above facilitates minimally invasive surgery by permitting a plurality of surgical elements to be introduced into a surgical site at one time. Once the surgical elements are present at the surgical site, they may be selectively used, as needed, by the surgeon, and may also be subsequently returned to the surgical carrier. In this manner, by eliminating the need for each element to separately be introduced into the surgical site, the length of time needed to perform the surgery can be reduced, as can the risk of inadvertent damage to the surgical port and/or tissue or organs surrounding the surgical site.

Figure 9A:
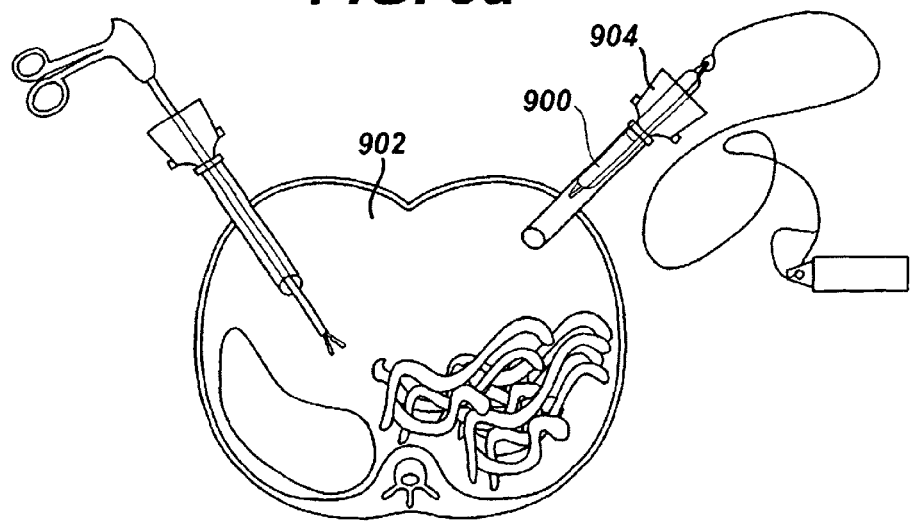
FIGS. 9a–9e illustrate various steps of a method for using a carrier equipped with a tether according to the present disclosure.
Figure 9B:
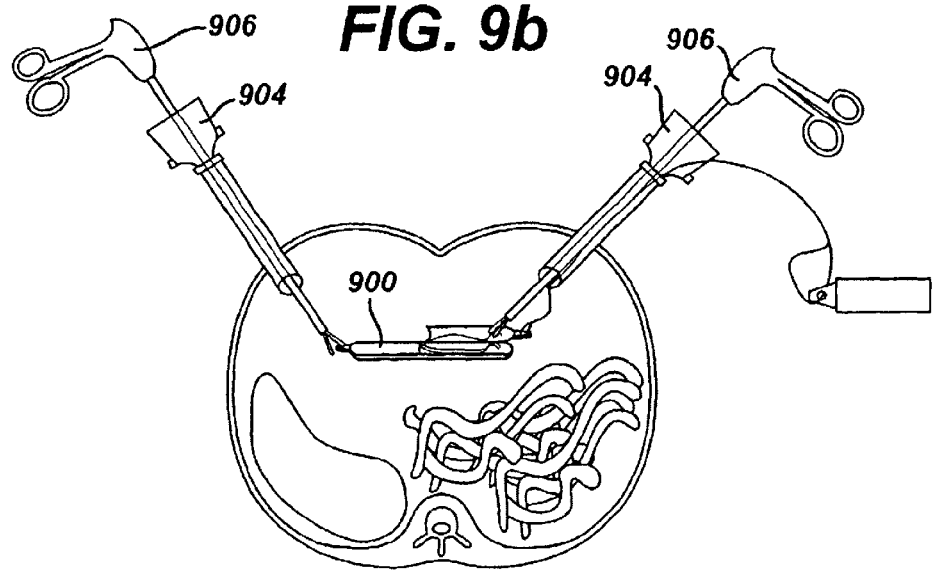
Figure 9C:
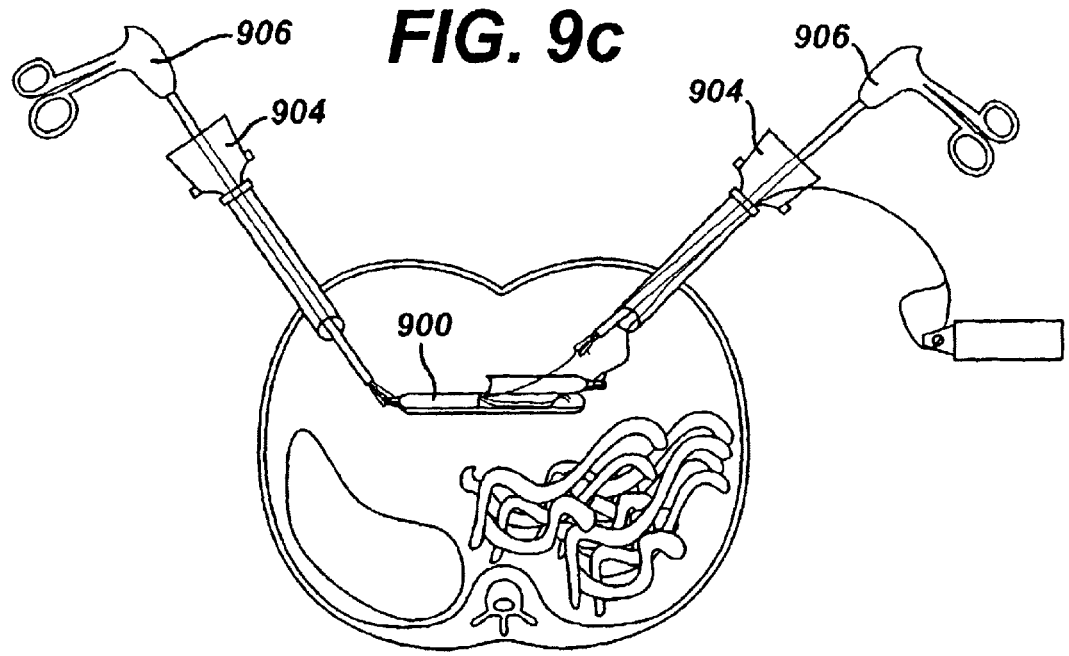
Figure 9D:
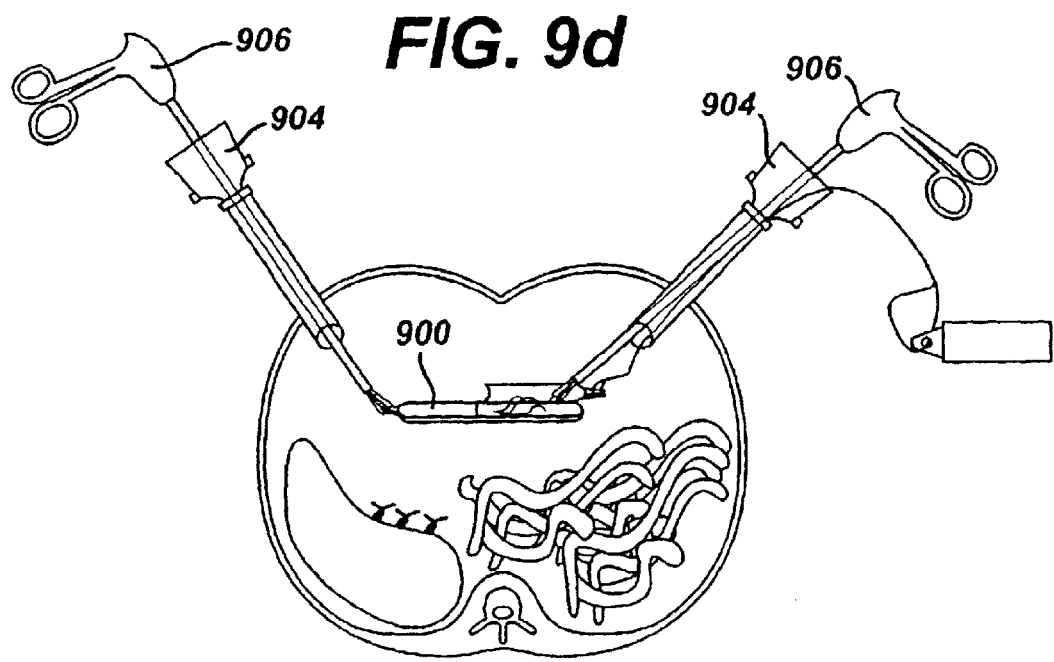
Figure 9E:
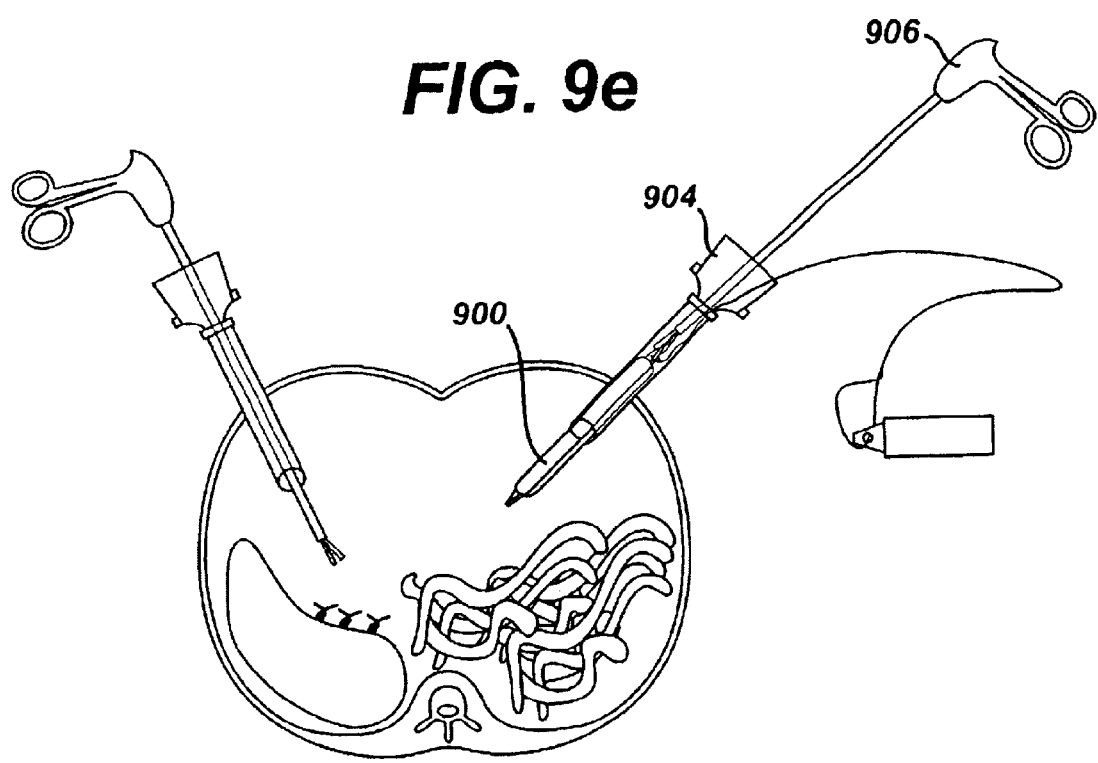

An improved method for performing minimally invasive surgery incorporating the above described surgical carrier will now be described in greater detail with reference to FIGS. 9a to 9e. First, the surgical carrier 900 containing a plurality of surgical elements that may be used for surgery is inserted into the surgical site 902 through a surgical port 904 as shown in FIG. 9a. Once inside the surgical site, if required, the carrier can be opened by the surgeon using any suitable standard surgical tool, such as a grasper 906, via the surgical port 904. The surgeon then proceeds to selectively remove a desired surgical element from the carrier, such as the suture shown in FIG. 9c, for use. When the surgeon has completed the necessary suturing, the needle can be re-parked in the carrier as shown in FIG. 9d. After all needed surgical elements have been used, the carrier is closed, and then removed from the surgical site by drawing it back up through the surgical port as shown in FIG. 9e. The attached tether can also be used to aid in the withdrawal of the carrier out of the surgical port. The tether is also a reminder that a device carrier is in use and must be withdrawn at the end of the surgery.

It will be apparent from the foregoing that, which particular forms of the invention have been illustrated and described, various modifications can be made without departing from the spirit and scope of the invention. Accordingly, it is not intended that the invention be limited, except as by the appended claims.

What is claimed is:

1. A surgical element carrier comprising:
a housing having a length, and outer diameter less than approximately 12 mm so as to allow insertion through a surgical port used in minimally invasive surgeries, the housing further comprising a first housing portion and a second housing portion movable relative to the first housing portion between a closed position wherein the surgical elements are substantially surrounded by the housing and an open position wherein the surgical elements are at least partially exposed and removable from the housing.

2. The surgical element carrier according to claim 1, wherein the housing is substantially cylindrical in shape, and the first housing portion is slidably engaged with the second housing portion and slidable relative to the second housing portion in a longitudinal direction between the closed and open positions.

3. The surgical element carrier according to claim 1, wherein the first housing portion is pivotably coupled with the second housing portion and pivotable between the open and closed positions.

4. The surgical element carrier according to claim 3, wherein the first housing portion is pivotably coupled to the second housing portion by at least one hinge, and wherein when the first housing portion is in the open position, the at least one hinge is biased toward the open position.

5. The surgical element carrier according to claim 1, wherein the housing is substantially cylindrical in shape.

6. The surgical element carrier according to claim 1, further comprising a plurality of sutures each having a needle attached thereto positioned within the housing.

7. The surgical element carrier according to claim 1, further comprising a plurality of surgical tips for an endoscopic surgical instrument positioned within the housing.

8. The surgical element carrier according to claim 1, wherein the housing is substantially cylindrical in shape and sufficiently flexible to permit bending along its length.

9. The surgical element carrier according to claim 1, further comprising a securing means at one end thereof for securing the surgical element carrier to a tissue within a patient's body.

10. The surgical element carrier according to claim 9, wherein the securing device is a clamp.

11. The surgical element carrier according to claim 9, wherein the securing device is a pointed element capable of penetrating tissue.

12. The surgical element carrier according to claim 1, further comprising a receiving element for receiving and maintaining in position the surgical elements.

13. The surgical element carrier according to claim 12, wherein the receiving element is comprised of a foam material.

14. The surgical element carrier according to claim 1, further comprising a flexible, filamentary tether element extending from one end thereof, the tether element having a length sufficient to extend from a surgical site within a patient's body, through the surgical port and to an exterior of the patient's body.

15. A surgical element carrier comprising:
a housing for transporting a plurality of surgical elements through a surgical port designed for use in a minimally invasive surgical procedure, the housing having a length and an outer diameter, wherein the outer diameter is less than approximately 12 mm and less than a diameter of said surgical port, wherein the housing is configured to partially surround the surgical elements, and has an aperture therein of a sufficient size and shape to enable the surgical elements to be removed from the carrier by an endoscopic surgical instrument.

16. The surgical element carrier according to claim 15, wherein the housing is substantially cylindrical in overall shape.

17. The surgical element carrier according to claim 15, wherein the surgical elements are sutures having needles attached thereto.

18. The surgical element carrier according to claim 15, wherein the surgical elements are instrument tips for an endoscopic surgical instrument.

19. The surgical element carrier according to claim 15, further comprising a grasping portion at one end thereof dimensioned to enable grasping of the surgical element carrier by an endoscopic surgical instrument.

20. A method for introducing a plurality of surgical elements into a surgical site during a minimally invasive surgical procedure comprising:
providing a surgical element carrier having a housing containing therein a plurality of surgical elements, the housing having a first housing portion and a second housing portion movable relative to the first housing portion between a closed position wherein the surgical elements are substantially surrounded by the housing and an open position wherein the surgical elements are at least partially exposed and removable from the housing, inserting the housing having the plurality of surgical elements therein into the surgical site through a surgical port;

selectively removing from at least one surgical element from the surgical element carrier while the surgical element carrier is within the surgical site;

using the at least on surgical element during the minimally invasive surgical procedure; and removing the surgical element carrier from the surgical site through the surgical port.

21. The method according to claim 20, further comprising, following the inserting step, opening the surgical element carrier to expose the surgical elements contained therein.

22. The method according to claim 21, wherein the housing further comprises a first housing portion and a second housing portion movable relative to the first housing portion, and wherein the first housing portion is slidably engaged with the second housing portion and slidable relative to the second housing portion between a closed wherein the housing substantially surrounds the surgical elements and an open position wherein the surgical instruments are at least partially exposed and can be removed from the housing.

23. The method according to claim 21, wherein the housing further comprises a first housing portion and a second housing portion movable relative to the first housing portion, and wherein the first housing portion is pivotably coupled with the second housing portion and pivotable relative to the second housing portion between a closed wherein the housing substantially surrounds the surgical elements and an open position wherein the surgical instruments are at least partially exposed and can be removed from the housing.

24. The method according to claim 20, wherein the surgical elements are sutures having a needle attached thereto.

25. The method according to claim 20, wherein the surgical elements are surgical tips for an endoscopic surgical instrument.

* * * * *